United States Patent
Visuri et al.

(10) Patent No.: US 6,491,685 B2
(45) Date of Patent: *Dec. 10, 2002

(54) LASER AND ACOUSTIC LENS FOR LITHOTRIPSY

(75) Inventors: Steven R. Visuri, Livermore; Anthony J. Makarewicz, San Ramon; Richard A. London, Orinda; William J. Benett, Livermore; Peter Krulevitch; Luiz B. Da Silva, both of Pleasanton, all of CA (US)

(73) Assignee: The Regents of the University of California, Oakland, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/516,999

(22) Filed: Mar. 1, 2000

(65) Prior Publication Data

US 2002/0058890 A1 May 16, 2002

Related U.S. Application Data

(60) Provisional application No. 60/122,728, filed on Mar. 4, 1999.

(51) Int. Cl.⁷ ............................................. A61B 17/22
(52) U.S. Cl. ........................................ 606/2.5; 606/128
(58) Field of Search ....................... 606/2.5, 127, 128, 606/15

(56) References Cited

U.S. PATENT DOCUMENTS

| | | | | |
|---|---|---|---|---|
| 4,932,954 A | * | 6/1990 | Wondrazek et al. | 606/2.5 |
| 4,968,314 A | * | 11/1990 | Michaels | 606/2.5 |
| 5,224,942 A | * | 7/1993 | Beuchat et al. | 606/2.5 |
| 5,324,282 A | * | 6/1994 | Dodick | 606/2.5 |
| 5,999,847 A | * | 12/1999 | Elstrom | 604/20 |

* cited by examiner

Primary Examiner—Ruth S. Smith
(74) Attorney, Agent, or Firm—L. E. Carnahan; Alan H. Thompson

(57) ABSTRACT

An acoustic focusing device whose acoustic waves are generated by laser radiation through an optical fiber. The acoustic energy is capable of efficient destruction of renal and biliary calculi and deliverable to the site of the calculi via an endoscopic procedure. The device includes a transducer tip attached to the distal end of an optical fiber through which laser energy is directed. The transducer tip encapsulates an exogenous absorbing dye. Under proper irradiation conditions (high absorbed energy density, short pulse duration) a stress wave is produced via thermoelastic expansion of the absorber for the destruction of the calculi. The transducer tip can be configured into an acoustic lens such that the transmitted acoustic wave is shaped or focused. Also, compressive stress waves can be reflected off a high density/low density interface to invert the compressive wave into a tensile stress wave, and tensile stresses may be more effective in some instances in disrupting material as most materials are weaker in tension than compression. Estimations indicate that stress amplitudes provided by this device can be magnified more than 100 times, greatly improving the efficiency of optical energy for targeted material destruction.

24 Claims, 2 Drawing Sheets

LASER AND ACOUSTIC LENS FOR LITHOTRIPSY

RELATED APPLICATION

This application relates to U.S. Provisional Application No. 60/122,728 filed Mar. 4, 1999, and claims priority thereof.

The United States Government has rights in this invention pursuant to Contract No. W-7405-ENG-48 between the United States Department of Energy and the University of California for the operation of Lawrence Livermore National Laboratory.

BACKGROUND OF THE INVENTION

The present invention relates to creation of a stress wave for causing material damage or destruction, particularly relevant to intracorporeal shock wave lithotripsy, particularly to the use of acoustic energy for lithotripsy, and more particularly to a device having a transducer tip for converting optical (laser) energy into acoustic energy to produce stress waves for local and targeted material destruction, primarily for medical applications such as lithotripsy.

The standard in the non-surgical treatment of biliary and urinary calculi, more commonly known as gallstones and kidney stones, is extracorporeal shock wave lithotripsy (ESWL). The procedure entails placing the patient in a water bath that holds an acoustic generator. The acoustic wave is focused through the water, usually with an ellipsoid reflector, and into the patient so that the focal point is at the location of the calculi. As the acoustic wave is focused it develops into a shock-like waveform. Several different commercial lithotripters are available, generating compressive pressures up to 120 MPa and tensile pressures of 10 MPa within a focal region ranging from about 0.2 $cm^3$ to 16 $cm^3$. Repeated pulses of the shockwave, as many as 2,000, break apart the calculi. The mechanism is not fully understood, but is most likely due to either cavitation near the stone surface or the development of stress and shear within the stone itself.

Ideally, ESWL would exclusively target the stones, under ultrasound or fluoroscopic guidance, without affecting the soft tissue near the focal point or the tissue lying in the path of the shockwave. In practice, however, complications arise that are related to the non-exclusive application of the shockwave. These complications include bleeding in almost all cases, common kidney failure, pancreatitis, bruise-like skin lesions at the site through which the shockwave passes, and in rare cases broken bones and heart arrhythmias[3]. Reducing the shockwave intensity to limit these complications reduces the efficiency of the devices to destroy stones. ESWL can not be used for patients (i) with predisposition to complications, (ii) obese patients or pediatric patients because the focal distance of the lithotripter cannot be adjusted to the site of the stone, or (iii) pregnant patients. In addition, ESWL fails to destroy some stones due to stone composition or mobility. Alternate techniques for removal of the stones must then be used.

The two most utilized alternatives are open surgical procedures and intracorporeal laser lithotripsy. The surgical technique is generally considered a last resort as it is costly and requires general anesthesia with hospital stays of up to a week, whereas ESWL is generally an outpatient procedure. Laser lithotripsy entails the transurethral guidance of an optical fiber through a flexible endoscope to the position of the stone. To create a radically expanding shock wave with a high enough intensity to break apart the calculi, the laser radiation must be of relatively high intensity. This high intensity beam can damage soft tissue. Successful calculi destruction is accomplished in a high percentage of patients, but damage to the bladder or ureter is relatively common, with perforations in about 6% of the cases.

The present invention utilizes laser energy directed through an optical fiber, as in laser lithotripsy, but additionally incorporates a shaped optical fiber tip, a transducer tip, or endpiece that converts optical (laser) energy into acoustic energy. The acoustic energy (stress waves) destroys targeted material with minimal damage to the surrounding (untargeted) tissue. The transducer tip or endpiece includes a material, such as an exogenous absorbing dye and an acoustic lens. Whether radiation absorption takes place in a transducer tip or in the ambient media, the generated stress waves travel through the transducer or endpiece and are focused by the acoustic lens to a spot outside the endpiece. The endpiece also serves to confine the laser radiation to eliminate the danger of direct absorption in soft tissue and subsequent perforation. Acoustic energy has little effect on soft tissue. The focusing of the acoustic wave will allow for both specific targeting of the shock wave to the stone and the generation of pressures equivalent to ESWL with a lower-cost laser than what is currently required for laser lithotripsy.

SUMMARY OF THE INVENTION

It is an object of the present invention to provide a more effective means for mechanically disrupting or damaging biological or non-biological materials.

A further object of the present invention is to provide a more effective lithotripsy procedure.

A further object of the invention is to provide a lithotripsy procedure that utilizes acoustic waves produced by laser radiation.

A further object of the invention is to provide a device for lithotripsy that utilizes optical energy to produce acoustic waves for the destruction of targeted material.

Another object of the invention is to utilize laser energy to produce acoustic waves for lithotripsy procedures.

Another object of the invention is to provide a lithotripsy technique that involves depositing laser radiation into an exogenous absorber contained within a capsule at the end of an optical fiber, which produces an acoustic wave that can be focused by an acoustic lens onto a target tissue or other material causing the destruction thereof.

Another object of the invention is to provide a device for lithotripsy that can convert compressive stress waves into a tensile stress wave for more effectively disrupting material.

Another object of the invention is to provide a device for lithotripsy that includes an acoustic lens such that the transmitted acoustic wave is shaped or focused.

Other objects and advantages of the present invention will become apparent from the following description and accompanying drawings. The present invention incorporates the use of a laser with a transducer tip that converts optical energy into acoustic energy to produce stress waves for local and targeted material destruction, primarily for medical applications, such as shock wave lithotripsy. Energy from a laser, such as a q-switched Nd:YAG laser, is directed into an optical fiber. A transducer tip is attached to the distal end of the optical fiber, and encapsulates an exogenous absorbing dye, for example. Under proper irradiation conditions (high absorbed energy density and short pulse duration) a significant stress wave is produced via thermoelastic expansion of the absorber and the stress wave is directed onto a targeted material for destruction thereof. Further, the transducer tip can be formed into an acoustic lens such that the transmitted acoustic wave is shaped or focused. In addition, the transducer tip can be constructed such that compressive stress waves can be inverted into a tensile stress wave. Tensile stresses may be more effective in disrupting material as most materials are weaker in tension than compression. Based on theoretical estimates, the stress amplitudes produced by this invention can be magnified more than 100 times, greatly improving the efficiency over that of an unfocused optoacoustic transducer.

BRIEF DESCRIPTION OF THE DRAWINGS

The accompanying drawings, which are incorporated into and form a part of the disclosure, illustrate embodiments of the invention and, together with the description, serve to explain the principles of the invention.

DETAILED DESCRIPTION OF THE INVENTION

Figure 1:
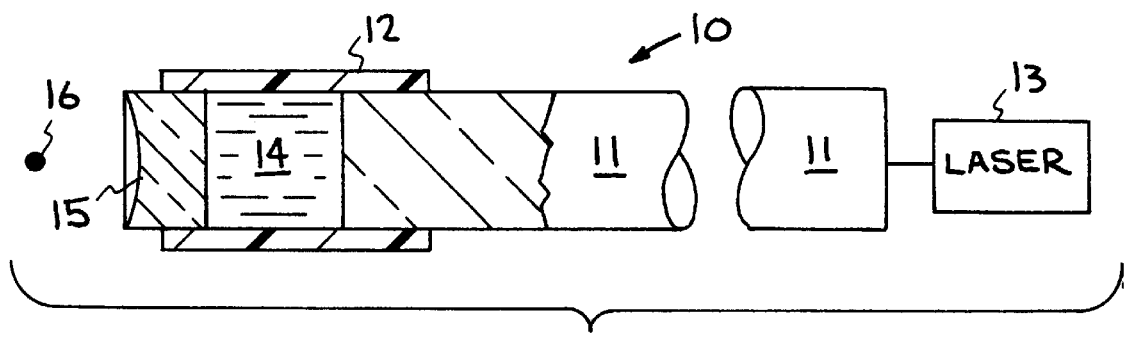
FIG. 1 is a schematic diagram of the fibertip and endpiece or transducer tip of the acoustic focuser made in accordance with the present invention.

The present invention involves a device particularly applicable for lithotripsy, and which utilizes a laser, an optical fiber for transmitting laser energy, and a transducer tip mounted to the distal end of the optical fiber for converting optical energy into acoustic energy, with the tip including an acoustic lens for focusing or shaping the shock waves emanating therefrom. Thus, the invention broadly involves a laser and acoustic lens for lithotripsy.

Absorbed radiation can produce acoustic waves under proper conditions. If the laser pulse duration, less than about 100 ns, is relatively short and the absorption depth is small, significant shock waves can be produced. These shock waves can be destructive, causing materials to fail through a combination of compression, tension, or shear stresses. Because laser radiation having a wave length of 200–3500 nm can be easily transmitted via optical fibers, this form of energy is uniquely suited to remote and minimally invasive delivery within the body. The destructive forces produced can be advantageous for a variety of medical applications. Lasers are currently used or under study to disrupt urinary and biliary stones, thrombus (blood clots) and plaque, and opthalmologic tissues. However, current applications usually rely on the direct absorption of laser radiation by the target. This reliance is inherently problematic, as the target properties vary between both applications and individuals. A technique that has many advantages and which constitutes the invention, is to deposit laser radiation into an exogenous absorber contained within a capsule at the end of an optical fiber. The absorber may be composed of a wide variety of gas, liquid, or solid materials that strongly absorb the incident radiation. For example, a high concentration of red dye, such as FDA red #2 (amaranth), dissolved in water absorbs 532 nm radiation very well; or water alone absorbs 2.94 radiation well. The resulting acoustic wave can be focused by an acoustic lens incorporated into the capsule. The advantages are: 1) control over the absorption characteristics, 2) increased magnitude of stresses with less required laser energy, 3) decreased thermal energy deposited into the target and surrounding tissues, 4) the ability to localize mechanical energy and pressure, and 5) the ability to alter the generated acoustic waveform.

The use of a transducer tip to convert optical energy into acoustic energy can solve some problems associated with current devices. Thermal energy can be removed from the human system more easily when laser energy is not directly deposited into the biological tissue. Further, the absorber could be flowed through the system to provide convective cooling. A transducer tip, particularly with focusing ability, can target specific tissues, sparing damage to surrounding tissues. In addition, a transducer tip allows better control and manipulation of the acoustic wave parameters: duration, magnitude, compressive/tensile, etc., via a controlled absorption environment. Thus, the use of optically-generated focused shock waves provides an efficacious, safe, and low-cost alternative to the currently available technology.

More specifically, the present invention incorporates the use of a laser to produce stress waves for local and targeted material destruction. A laser, such as q-switched ND:YAG laser, is directed into on optical fiber having a diameter in the range of 0.1–1.0 mm. A transducer tip is attached to the distal end of the optical fiber, and encapsulates an exogenous absorbing dye. Under irradiation involving high absorbed energy density (0.1 to 100 J/g) and short pulse duration (0.3 ns to 0.5 $\mu$s), a significant stress wave is produced via thermoelastic expansion of the absorber. Other methods of absorbing laser energy and creating acoustic waves are possible, for example; absorbing directly into ambient media (urine, blood, saline, etc.); absorbing directly into transducer material; abating the transducer material; etc. The absorption parameters and transducer geometry can be manipulated such that resulting stress waves are directed. In this manner, tissues can be selectively affected while sparing surrounding tissue. Stress waves can be forward-, side-isotropically-,or cylindrically-directed. Compressive stress waves can be reflected off a high density/low density interface to invert the compressive wave into a tensile stress wave. Tensile stresses may be more effective in disrupting material as most materials are weaker in tension than compression. Further, the transducer tip can be formed into an acoustic lens such that the transmitted acoustic wave is shaped or focused. Alternatively, the fiber tip itself may be shaped to focus the stress wave formed by depositing radiation into the native ambient fluids. Theoretical estimates indicate that stress amplitudes can be magnified more than 100 times, greatly improving the efficiency of the optical energy. This invention also provides a monetary advantage, allowing the use of lower cost lasers. Thus, the use of optically-generated focused shock waves, produced in accordance with the present invention, provides an efficacious, safe, and low-cost alternative to the currently available technologies and methods.

Referring now to the drawings, FIG. 1 is a schematic illustration of the invention and comprises a device generally indicated at 10 comprising a flexible optical fiber 11 having a transducer tip or endpiece 12 mounted to a distal end and a laser 13 operatively connected to the proximal end, with the transducer tip 12 including an absorber 14 and an acoustic lens 15 which focuses shock waves onto a focal point 16. The device 10 (optical fiber 11 and transducer tip 12) are introduced intracorporeally through the urethra and bladder, utilizing the flexible optical fiber 11 to deliver laser radiation from laser 13 to the absorber 14. The laser radiation is deposited within the absorber 14 and if the laser pulse duration is sufficiently short, a stress wave is created through thermoelastic expansion. The wave travels through the fluid or absorber 14 and is focused by the acoustic lens 15 to a spot or focal point 16 outside the tip 12. The tip or endpiece 12 also serves to confine the laser radiation to eliminate the danger of perforation of the surrounding tissue. The focusing of the acoustic wave will allow for both specific targeting of the shock wave to the stone and the generation of pressures equivalent to current extracorporeal shock wave lithotripsy (ESWL) with a lower-cost laser than that which is required for currently available laser lithotripsy.

Thermoelastic generation of stress waves generally requires short laser pulse durations and high energy density. Thermoelastic stress waves can be formed when the laser pulse duration is shorter than the acoustic transit time of the material:

$$t_c = d/c_s$$

where in which d=absorption depth or spot diameter, whichever is smaller, and $c_s$=sound speed in the material. The stress wave due to thermoelastic expansion travels at the sound speed (approximately 1500 m/s in water or soft tissue). Shock waves are used in ophthalmology to perform intraocular microsurgery and photodisruptive procedures as well as in lithotripsy to fragment stones. We have explored a variety of transducers that can efficiently convert optical to mechanical energy. One such class of transducers allows a shock wave to be focused within a material such that the stress magnitude can be greatly increased compared to conventional geometries. Some transducer tips could be made to operate regardless of the absorption properties of the ambient media. The size and nature of the devices enable easy delivery, potentially minimally-invasive procedures, and precise tissue-targeting while limiting thermal loading. The transducer tips may have applications in lithotripsy, ophthalmology, drug delivery, and cardiology.

Figure 3:
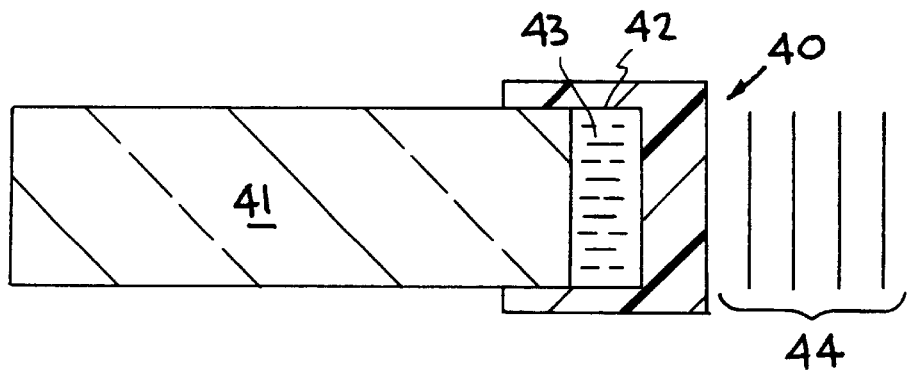
FIGS. 3–7 illustrate embodiments of the transducer tip, with FIGS. 3–6 illustrating the acoustic wave form emanating from the tip.

The geometry of acoustic lenses was studied with respect to focusing laser-produces stress waves. Laser radiation was supplied by a frequency doubled Nd:YAG laser (model 250–10 GCR, Spectra Physics, Mountain View, Calif.) emitting 5 ns-duration pulses of 532 nm light. The laser radiation was coupled into quartz optical fibers having diameters ranging from 0.2–1.0 mm. Several transducer focusing tips of differing materials and dimensions were produced and tested for their coupling efficiency and focusing ability. A variety of transducer tips could be produced, ranging from shaping the fiber tip itself, to complicated mechanical devices. The basic design of one transducer is shown in FIG. 3. This tip has a cavity for holding an absorbing media such as a dyed liquid. The laser-produced stress wave is formed in the absorbing media and transmitted to the transducer tip which is shaped to focus the stress wave.

Figure 2:
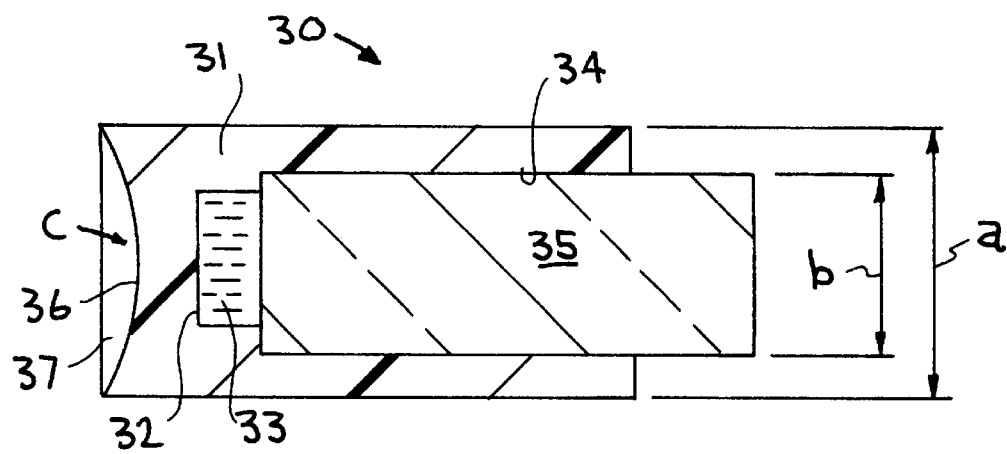
FIG. 2 illustrates another embodiment of the invention wherein the acoustic lens is formed in one end of a housing defining the transducer tip and within which is the absorber (dye) and end of the optical fiber.

The transducer of FIG. 2, indicated generally at 30, comprises a housing 31 defining a cavity 32 containing a dye 33, a countersink 34 within which an optical fiber 35 is mounted, and a concave end section 36 defining a lens 37. The housing 31 may be constructed of glass, plastic, rubber, metal, or ceramic. By way of example the housing 31 has an outer diameter of 1.3 mm indicated by arrow 2, with optical fiber 25 having an outer diameter of 1 mm indicated by arrow b, and with the concave end section 36 having a radius R of 1.6 mm as indicated by arrow c.

We have demonstrated the potential of focusing laser-produced stress waves. These stress waves may be used for applications of targeted tissue disruption such as in lithotripsy, interventional cardiology, or ophthalmology. In addition, less destructive stress waves may be beneficial in drug delivery. The use of transducer tips incorporating an absorber allows for predictable and reproducible events independent of the absorption of the ambient media. The incorporation of tips and a focused geometry also protects the optical fiber from stress induced damage. Further, the increased intensity at the focus enables one to use less laser energy to achieve the same intensity as unfocused stress waves, reducing the non-beneficial thermal load.

Initial transducers were made of aluminum for ease of machining. However these materials have significantly different acoustic impedances compared to tissue, water, or blood. The acoustic impedances of the interfacing materials determine the intensity of the reflected and transmitted stress wave. The reflection coefficient is given by:

ti $R=(1-z_1/z_2)/(1+z_1/z_2)$ in which z=acoustic impedance of the media. Acoustic impedances of water and blood are 1.48 and 1.61, respectively, while aluminum is 17 g/cm²s, resulting in a reflection coefficient greater than 83%. Subsequent transducers were produced from polystyrene (z=2.94 g/cm²s) to better match impedances (R=29%). The theoretical diffraction limited focal spot radius (84% of energy) is given by:

$$r_0 = 0.61 \lambda f/R$$

in which $\lambda$=wavelength of sound, f=focal length of lens, and R=initial radius. The focal length of the acoustic lens is given by:

$$f = R/(1-c_L/c_s)$$

in which $c_L$=liquid sound speed and $c_s$=solid sound speed. Using practical values ($\lambda$=12 $\mu$m, f=1 mm, R=200 $\mu$m) a spot radius of less than 40 $\mu$m is predicted. Taking into consideration the effective focal depth, this could increase the shock intensity at the focus by approximately 10 times that at the transducer tip. Transducers can be further improved by better impedance matching materials and potentially absorbing into the transducer material directly.

FIGS. 3–7 illustrate transducer embodiments designed to generate various types of acoustic waves. Similar components in FIGS. 3–7 embodiment have been given corresponding reference numerals.

Figure 4:
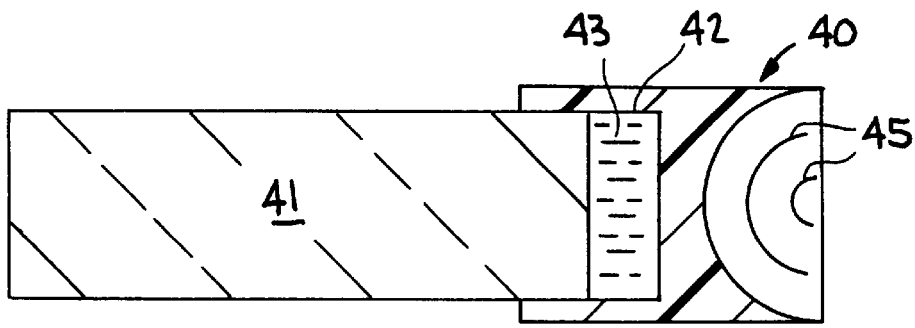
Figure 5:
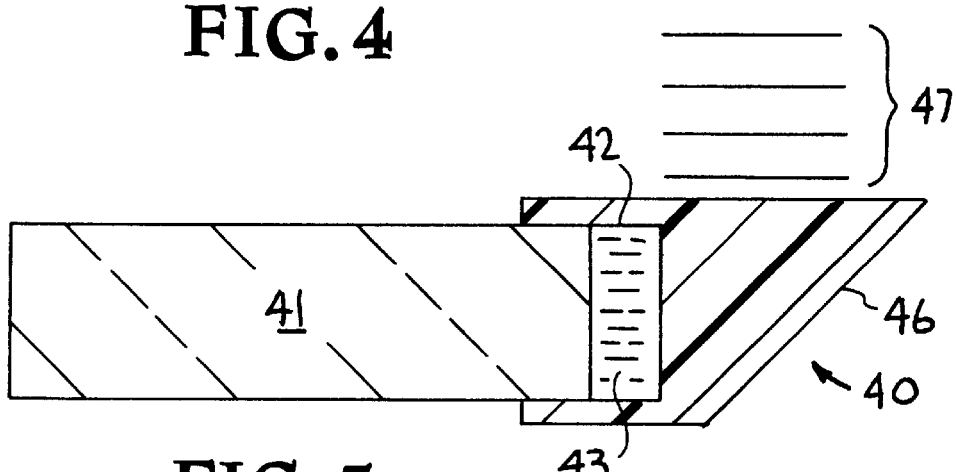

FIG. 3 illustrates a transducer tip generally indicated at 40, mounted to an end of an optical fiber 41 and having a cavity 42 containing a dye 43. The tip 40 is provided with a flat end surface for producing a plane wave indicated at 44. In FIG. 4, the end of tip 40 is a concave configuration producing a focused hemispherical wave indicated at 45. In FIG. 5, the end of tip 40 is of a tapered configuration having a member 46 mounted thereto whereby the reflected wave 47 is an inverted (tensile) wave.

Figure 6:
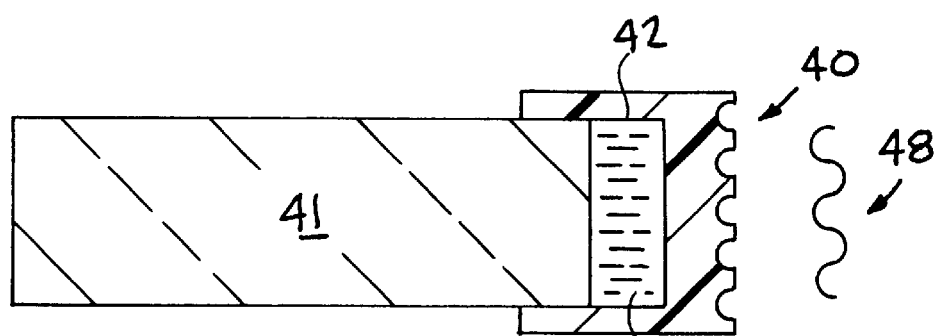
Figure 7:
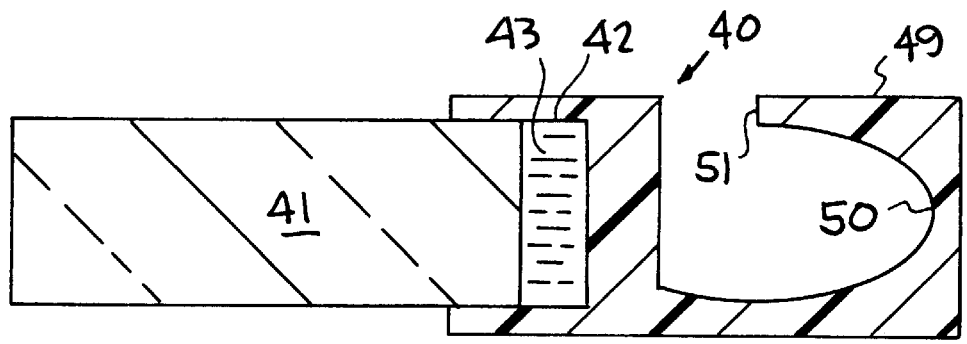

In FIG. 6, the end of tip 40 is of a multi-faceted configuration which produces a complex interference, multi-faceted wave pattern indicated at 48. In FIG. 7, a member 49 is attached to the end of tip 40 and includes an elliptical cavity 50 and opening 51, whereby an inverted elliptical reflection wave indicated by arrow 52 is produced emanating from opening 51.

It has thus been shown that the present invention provides a device which involves a laser system, an optical fiber, and a transducer tip mounted to the distal end of the optical fiber and containing therein an exogenous absorber, such as a dye, whereby laser radiation is converted to acoustic waves capable of the disruption of materials at remote locations. The transducer tip may include or be configured to define an acoustic lens whereby the acoustic waves are focused or shaped to be directed onto a specific point or target material.

The device is particularly applicable for various medical applications. In addition, the transducer tip may be constructed to convert compressive stress waves to tensile stress waves.

While particular embodiments, materials, parameters, etc., have been described and/or illustrated to exemplify and teach the principles of the invention, such are not intended to be limiting. Modifications and changes may become apparent to those skilled in the art, and it is intended that the invention be limited only by the scope of the appended claims.

What is claimed is:

1. A device, comprising:
    an optical fiber for transmitting laser energy,
    a transducer mounted at a distal end of said optical fiber,
    said transducer consisting of an absorber located adjacent an end of said optical fiber, and an acoustic lens located adjacent said absorber,
    whereby laser energy transmitted through said optical fiber is directed onto said absorber to produce an acoustic wave for material destruction.

2. The device of claim 1, wherein said acoustic lens is located in an outer end of said transducer.

3. The device of claim 1, wherein said acoustic lens is integral with said transducer.

4. The device of claim 1, wherein said absorber comprises a means for converting compressive stress waves into tensile stress waves.

5. The device of claim 1, wherein said acoustic lens includes a housing, said housing having a cavity therein containing said absorber, and having a countersink into which the distal end of said optical fiber is mounted.

6. The device of claim 5, wherein said absorber is composed of a dye.

7. The device of claim 5 wherein said absorber is composed of a fluid.

8. The device of claim 1, wherein said absorber comprises an exogenous absorbing dye.

9. The device of claim 1, in combination with a laser capable of producing short duration, high energy pulses, said pulses being transmitted through said optical fiber onto said absorber.

10. The combination of claim 9, wherein said laser is Nd:YAG laser.

11. The combination of claim 9, wherein said laser pulses are of a wavelength of about 532 nm at a duration of about 5 ns.

12. The combination of claim 9, wherein said optical fiber has a diameter ranging from about 0.1 mm to about 1.0 mm.

13. The combination of claim 9, wherein said short duration pulse is less than about 100 ns, and wherein said energy pulses are a wavelength of 200–3500 nm.

14. A method for producing acoustic waves by absorbed laser radiation, comprising:
    providing a source of laser radiation,
    providing an optical fiber,
    providing a transducer containing an absorber,
    providing an acoustic lens for focusing or shaping the acoustic waves,
    positioning the acoustic lens adjacent the absorber, and
    directing laser radiation through the optical fiber and onto the absorber for producing acoustic waves.

15. The method of claim 14, wherein providing a source of laser radiation is carried out by providing a laser having a pulse duration of about less than 100 ns.

16. The method of claim 15, additionally including providing a laser having an energy density of about 0.1 to 100 J/g.

17. The method of claim 14, additionally including providing the absorber from material selected from the group consisting of dyes, and opaque materials.

18. The method of claim 14, wherein the acoustic wave is directed onto a calculus for the purpose of lithotripsy.

19. A device for converting laser radiation into acoustic energy, comprising;
    an optical fiber for transmitting laser radiation,
    a transducer mounted to a distal end of said optical fiber,
    an absorber contained in said transducer and located adjacent said distal end of said optical fiber, and
    an acoustic lens located adjacent said absorber for focusing or shaping acoustic waves.

20. The device of claim 19, wherein said absorber comprises a means for converting compressive stress waves into a tensile stress wave.

21. The device of claim 19, wherein said acoustic lens is mounted to said transducer.

22. The device of claim 19, wherein said acoustic lens is located in said transducer.

23. The device of claim 19, wherein said absorber is composed of material selected from the group consisting of dyes and opaque materials.

24. A device, comprising:
    an optical fiber for transmitting laser energy,
    whereby laser energy transmitted through said optical fiber is directed into an ambient absorbing material located adjacent said optical fiber to produce acoustic waves for material destruction,
    wherein a distal end of said optical fiber includes an acoustic lens so as to focus the acoustic waves at a distance from a tip of said optical fiber.

* * * * *